United States Patent [19]

Berger et al.

[11] Patent Number: 5,406,845
[45] Date of Patent: Apr. 18, 1995

[54] INSTRUMENT FOR MEASURING A MUSCULAR FORCE

[76] Inventors: Antoine Berger, Pommerois, Saint-Victor-Sur-Loire, F-42000 Saint Etienne; Jean-Claude Barlerin, 48 Bis Rue Gambetta, F-42170 Saint-Just-Saint-Rambert, both of France

[21] Appl. No.: 125,298

[22] Filed: Sep. 22, 1993

Related U.S. Application Data

[63] Continuation of Ser. No. 769,543, Oct. 1, 1991, abandoned.

[30] Foreign Application Priority Data

Oct. 1, 1990 [FR] France .................. 90 12375

[51] Int. Cl.⁶ .................. G01L 1/00; G01L 5/00
[52] U.S. Cl. .................. 73/379.09; 73/379.08
[58] Field of Search .................. 73/379, 380, 381, 379.01, 73/379.06, 379.08, 379.09; 482/901, 902, 903; 128/25 R

[56] References Cited

U.S. PATENT DOCUMENTS

| | | | |
|---|---|---|---|
| 4,544,154 | 10/1985 | Ariel | 73/379.09 |
| 4,607,841 | 8/1986 | Gala | 73/379 |
| 4,613,130 | 9/1986 | Watson | 73/379 |
| 4,934,694 | 6/1990 | McIntosh | 73/379 |

Primary Examiner—Richard E. Chilcot, Jr.
Assistant Examiner—R. Biegel
Attorney, Agent, or Firm—Eckert Seamans Cherin & Mellott

[57] ABSTRACT

An instrument for measuring a muscular force particularly suited for the re-education and/or development of a muscle belonging to an upper and/or lower limb of the human body. A linearly displaceable element is coupled to a displacement device operable to continuously reciprocate the element with adjustable speed and travel. The displacement element is mounted such that a part of the human body can exert a muscular force (F1) upon the element. For example the element can be formed with one or more impressions to create an artificial climbing grip. The displacement device is coupled to a control center capable of, displaying a force threshold corresponding to a force of defined and variable intensity, operating the displacement device if the intensity of the force exerted on the element (F1) is greater than or equal to the displayed threshold value, measuring the force supplied, measuring the displacement, speed and travel of the element, measuring the duration of the force (F1).

17 Claims, 2 Drawing Sheets

INSTRUMENT FOR MEASURING A MUSCULAR FORCE

This is a continuation of application Ser. No. 07/769,543, filed Oct. 1, 1991, now abandoned.

The invention more particularly concerns an instrument for the re-education and/or development of a muscle, particularly belonging to an upper and/or lower limb of the human body.

Numerous instruments designed to perform such functions are known. In general, the majority of these instruments use means of the spring type or others capable of creating an adjustable or non-adjustable antagonist force which it to be overcome. The intensity of the force exerted can be displayed on screens. In addition, as a function of the aim sought, these instruments can operate either statically or dynamically.

One is familiar with instruments containing an element acted upon by a part of the human body in order to undergo a pull and/or thrust, with this element being controlled by means indicating the intensity of the force exerted. This state of the art can be illustrated by the teaching of Pats. WO-A-8801185, EP-A-0.151,066 and EP-A-0.267.271.

Irrespective of the design of this type of instrument, after relaxing the force exerted, a reaction force is created which is transmitted to the muscle concerned to a greater or lesser degree. However, in certain cases, particularly for training specific muscles, it is important that the muscle should not be subjected to any force after relaxing the force exerted. This is the case with the hand muscles, in particular, when climbing.

Quite obviously, this problem is posed more particularly when measuring a force dynamically.

In order to overcome the problems of known muscle-building and/or re-education instruments, the problem which the invention proposes to solve is to measure a force without subjecting the muscle concerned to any reaction force.

The problem posed of measuring the muscular force without subjecting the muscle to a reaction force when the force is relaxed, in the case of dynamic operation, is solved in that the element is mounted with displacement capacity while being connected to a device capable of subjecting the said element to a continuous reciprocating motion with adjustable speed and travel only when a defined and adjustable threshold value corresponding to the intensity of a force is reached, with the said element remaining immobile or stopping when the said value is not reached.

The problem posed of displacing the moving element only when the force exerted on it is at least equal to the value of a defined threshold, which has the effect, conversely, of causing the said moving element to stop as soon as the force is relaxed, is solved in that the device comprises a measuring assembly formed by a motor mounted with limited displacement capacity and coupled to a fixed sensor element connected to a control centre, with the said motor having fittings to ensure or prevent the displacement of the element or elements subjected to the pull and/or thrust.

This problem is solved to advantage in that the motor fittings consist of a worm engaged in a part of a support acting as a nut and equipped with the element or elements.

The support is mounted with linear displacement capacity and guided on a base.

As a function of the muscle to be re-educated or developed, the support equipped with the element or elements is mounted with displacement capacity in relation to a fixed supporting base plate arranged to take the part of the human body concerned.

Taking into account the problem posed which is to be solved, the control centre comprises a combination of different modules capable of fulfilling he following essential functions:
- displaying a force threshold corresponding to a force of defined and variable intensity;
- starting the motor if the value of the force exerted on the element is at least equal to or more than the threshold value displayed, causing displacement according to a continuous reciprocating motion of the support equipped with the element or elements;
- measuring the force supplied;
- measuring the displacement speed and travel;
- measuring the duration of the force.

Figure 1:
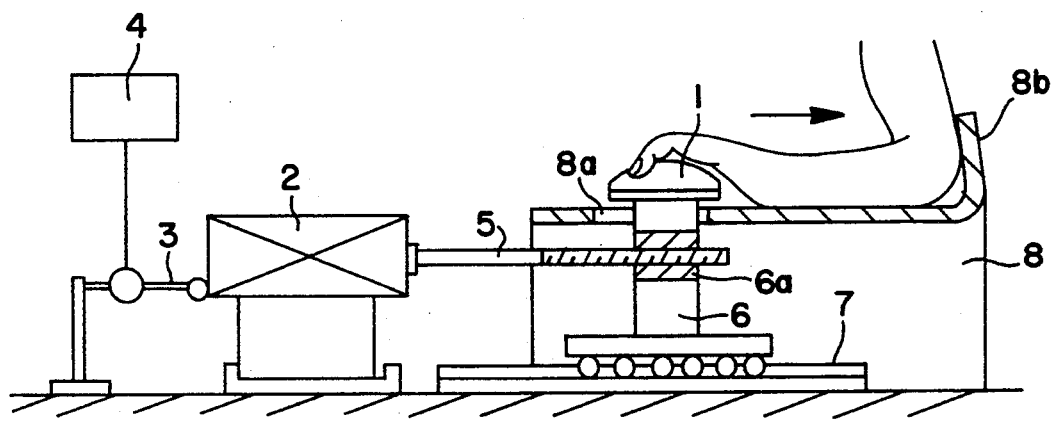
FIG. 1 is a schematic sectional view showing an embodiment of the measuring instrument employing the principle on which the invention is based. In this figure, the element acted upon by a part of the human body is in the rest position.
Figure 2:
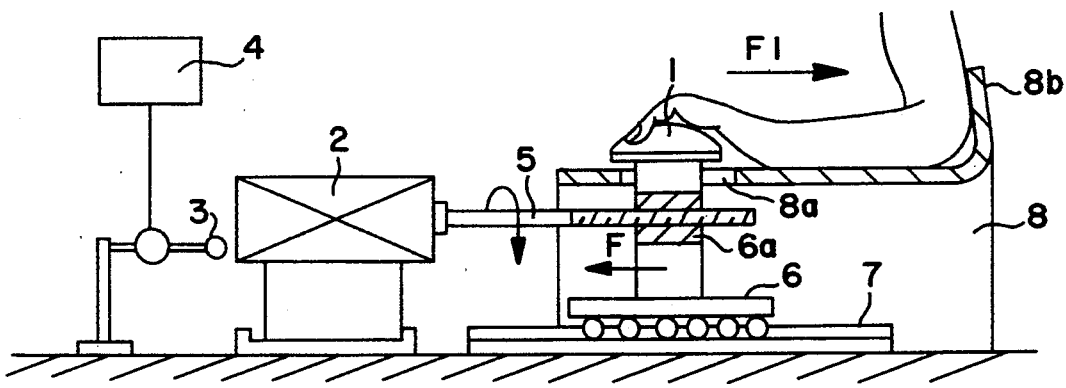
FIG. 2 is a view similar to FIG. 1 showing the displacement of the moving element when a force is exerted on the latter and when the intensity of this force is greater than a predetermined threshold value.
Figure 3:
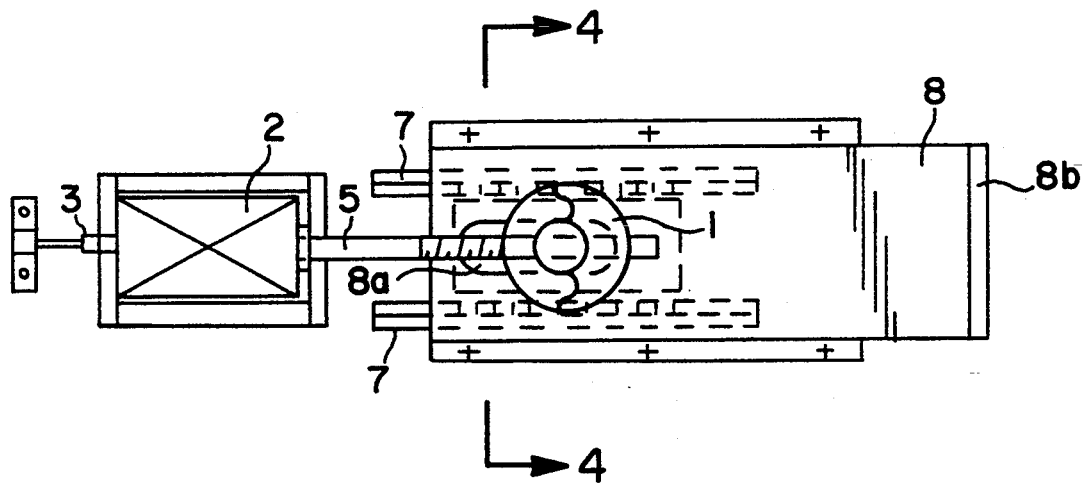
FIG. 3 is a plan view corresponding to FIG. 1.
Figure 4:
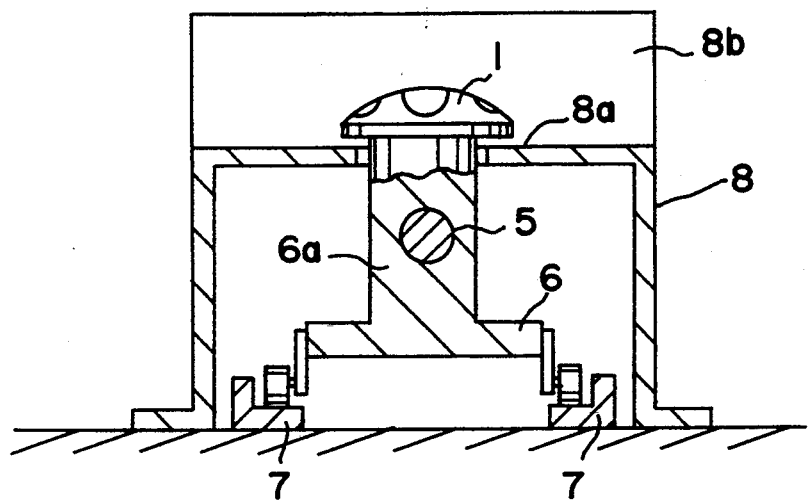
FIG. 4 is a sectional view considered along line 4—4 in FIG. 3.

The measuring instrument according to the invention comprises at least one element (1) designed to be acted upon by a part of the human body in order to undergo a pull and/or thrust. As will be indicated in the following description, this element (1) can have different embodiments as a function of the envisaged applications and the part of the human body concerned which can be constituted by part of one of the upper or lower limbs, for example.

This element (1), irrespective of its embodiment, is controlled by means capable of indicating the intensity of the force exerted.

In a preferred embodiment, he element (1) is mounted with displacement capacity, particularly for linear motion, while being connected to a device capable of causing its displacement according to a continuous reciprocating motion by creating a reaction force (F) opposed to the force (F1) exerted on the said element. This device is also designed to ensure the displacement of the element (1) according to adjustable speed and travel.

More particularly, according to a basic characteristic of the invention, the displacement of the element (1) is permitted only when the force (F1) to which it is subjected is higher than or at least equal to a defined, adjustable threshold value. When this threshold value is not reached, the element (1) remains immobile or else stops immediately when the intensity of the force (F1) exerted again falls below this threshold value.

Essentially, and in the embodiment illustrated, the device, to which the element (1) is connected and permitting its displacement only under the conditions cited above, comprises a measuring assembly consisting of a motor (2) mounted with limited displacement capacity whilst being coupled to a fixed sensor element (3). This sensor element (3), of any known and suitable type and whose design depends on the nature of the force exerted, i.e. either a thrust or a pull, is connected to an electronic control centre (4).

The motor (2) is also designed to ensure the displacement or non-displacement of the element or elements subjected to the pull and/or thrust, according to a continuous reciprocating motion. For example, the motor shaft drives a worm (5) engaged in a part (6a) of a support (6) holding the element (1). This part (6a) acts as a nut and its rotation is immobilised such that the driving of the worm (5) by the motor (2) ensures the concomitant displacement of the whole of the support. The support (6) is mounted with linear displacement capacity guided on a base (7).

This method of displacement by a worm and nut system as defined ensures a considerable reduction and permits irreversibility of the motion. However, this system must not be considered restrictive. In fact, any other system causing a linear displacement, such as a rack and pinion, hydraulic cylinder or others, can enter within the scope of the invention.

As indicated, the displacement device causes reciprocation of the moving element (1), with the travel and speed of this motion being adjustable by the operator.

The support (6) for the element (1) is mounted to advantage with displacement capacity in relation to a fixed supporting base plate (8) designed to take the part of the human body concerned. For example, the support (1) moves in a hole (8a) in the supporting base plate (8). As indicated, this supporting base plate possesses all types of fittings making it possible to position the part of the human body concerned and intended to act upon the element (1) with thrust or pull.

The control centre (4) comprises a combination of different modules capable of providing the following essential functions:
- displaying a force threshold corresponding to a force of defined and variable intensity;
- starting the motor (2) if the intensity of the force (F1) exerted on the element (1) is at least equal to or more than the threshold value displayed, thus, under the action of the worm (5), causing displacement of the support (6) according to a continuous reciprocating motion;
- measuring the force supplied;
- measuring the displacement speed and travel of the element (1);
- measuring the duration of the force (F1) applied.

The measuring instrument as described finds numerous applications in the re-education or development of a muscle.

Amongst other, the instrument finds a particularly advantageous application in climbing training with regard to the hand muscles which are highly stressed in this type of sport. In this case, the element (1) is formed by a shape having different impressions to form an artificial climbing grip. The supporting base plate (8) has a section in relief (8b) acting as a stop and making it possible to prop up the forearm and/or of the body at the level of the armpit and shoulder, when the hand seizes the climbing grip (1).

This results in the following cycle:

The user displays the value of the threshold corresponding to the intensity of the pull which he wishes to exceed. After positioning his forearm on the corresponding part of the base plate (8) and arranging the fingers of his hand in the impressions of the climbing grip (1), the user exerts on the said grip a pull (F1), the effect of which is to act upon the sensor (3). If, as a function of the state of the sensor (3), this force (F1) is below the threshold value displayed, the motor (2) is not driven and, consequently, the support assembly (6) with the grip (1) is immobile (FIG. 1). If this force (F1) reaches and exceeds the threshold value displayed, the motor (2) is driven, creating concomitantly, under the influence of the worm (5), the displacement of the support (6) equipped with the grip (1), creating a reaction force (F) opposed to the pull exerted (F1). The displacement of the support (6) and, consequently, of the grip (1) takes place according to a continuous reciprocating movement, the travel and speed of which can be adjusted by the user.

When the force is in the direction of displacement of the support, it should be noted that the muscles work concentrically. Conversely, when the force is opposed to the direction of displacement, the muscles work eccentrically.

As soon as the user relaxes his force, or the intensity of the force (F1) falls below the threshold value displayed, the motor (2) is no longer driven and, consequently, the support (6) with the grip (1) is stopped immediately.

Naturally, the whole of the measuring instrument as illustrated and described can have different arrangements as a function of the type of application envisaged.

The benefits emerge clearly from the description; in particular, one emphasises and recalls the possibility of exerting a muscular force and of no longer subjecting the muscle concerned to any reaction force after relaxing the said force exerted.

We claim:

1. A muscle training device, comprising:
   at least one user engageable element movably mounted relative to a base via a displaceable mounting means, and defining a displacement over which a user can exert a force against the user engageable element;
   a measurement device coupled between the at least one user engageable element and the base, including sensor means operable to sense a level of said force exerted by the user;
   control means coupled to the measurement device, operable to compare the level of said force with a threshold force;
   drive means responsive to the control means, the drive means displacing the at least one user engageable element relative to the base, against said force, in a linear reciprocating motion; and,
   coupling means, coupling the drive means with the at least one user engageable element, for alternating between driving the at least one user engageable element in an in-motion state and preventing the displacement of the at least one user engageable element in opposition to any force exerted by the user, thereby fixing the at least one user engageable element in an immobile state;
   the control means including switching means connected to the drive means for switching the drive means between on and off, which correspondingly results in the at least one user engageable element being reversibly switched between the in-motion state and the immobile state;
   wherein the control means activates the drive means when the force exerted by a user on the at least one user engageable element is at least equal to the threshold force, whereupon the at least one user engageable element is accordingly switched to the in-motion state, and the control means deactivates the drive means when said force is less than the threshold force, whereupon the at least one user engageable element is automatically switched to the immobile state, which results in the user not being subjected to any force via the at least one user engageable element once the user relaxes the force.

2. The muscle training device of claim 1, wherein the drive means and measurement device comprise a motor mounted for a limited displacement relative to the base, the measurement device including a force sensor fixed relative to the base for sensing displacement of the motor, the threshold force being determined by displacement of the motor toward and away from the fixed force sensor.

3. The muscle training device of claim 2, wherein the motor is mounted to the at least one user engageable element via fittings including a worm engaged with a part of the user engageable element acting as a nut on the worm.

4. The muscle training device of claim 1, wherein the at least one user engageable element is displaceably mounted relative to a supporting plate arranged for receiving a part of the user's body to act on the at least one user engageable element.

5. The muscle training device of clam 1, further comprising means for adjusting at least one of a speed and a displacement of the at least one user engageable element by the user.

6. The muscle training device of claim 1, further comprising means for adjusting the threshold force by the user.

7. The muscle training device of claim 1, wherein the control means for:
displaying a defined threshold force value;
measuring the force exerted on the at least one user engageable element;
measuring the speed and travel of displacement of the at least one user engageable element; and,
measuring the duration of force exerted on the at least one user engageable element.

8. The muscle training device of claim 1, wherein the at least one user engageable element is a hand grip.

9. The muscle training device of claim 1, wherein displacement of the user engageable element is linear.

10. The muscle training device of claim 1, wherein the drive means comprises a motor; and,
the coupling means comprises a worm turned by the motor and part of he at least one user engageable element that is engaged with the worm and acts as a nut on the worm;
wherein the worm and nut-part provide reduction in an output of the motor to the extent that, while the motor is switched off, the user is prevented from displacing the at one user engageable element by the pull and/or thrust force.

11. A training device for hand muscles of a user, comprising:
a hand grip movably mounted relative to a base via a displaceble mounting means, and defining a displacement over which the user can exert a force against the hand grip relative to the base;
a measurement device coupled between the hand grip and the base, including sensor means operable to sense a level of said force exerted by the hand muscles of the user;
control means coupled to the measurement device, operable to compare the level of said force with a threshold force;
drive means responsive to the control means, the drive means displacing the hand grip relative to the base, against said force, in a linearly reciprocating motion; and,
coupling means, coupling the drive means with the hand grip, for alternating between the hand grip in an in-motion state and preventing the displacement of the hand grip in opposition to any force exerted by the user, thereby fixing the hand grip in an immobile state;
the control means including switching means connected to the drive means for switching the drive means between on and off, which correspondingly results in the hand grip being reversibly switched between he in-motion state and the immobile state;
wherein the control means activates the drive means when the force exerted by a user on the hand grip is at least equal to the threshold force, whereupon the hand grip is accordingly switched to the in-motion state, and the control means deactivates the drive means when said force is less than the threshold force, whereupon the hand grip is automatically switched to the immobile state, which results in he user not being subjected to any force via the hand grip once the user relaxes the pull and/or thrust force.

12. The muscle training device of claim 11, wherein the drive means and measufement device comprise a motor mounted for a limited displacement relative to the base, the measurement device including a force sensor fixed relative to the base for sensing displacement of the motor, the threshold force being determined by displacement of the motor toward and away from the fixed force sensor.

13. The muscle training device of claim 12, wherein the motor is mounted between the base and the hand grip via fittings including a worm and a nut on the worm.

14. The muscle training device of claim 11, further comprising a supporting plate arranged for receiving a part of the user's body to be fixed relative to the base.

15. The muscle training device of claim 11, further comprising means for adjusting at least one of a displacement and a travel of the hand grip by the user.

16. The muscle training device of claim 11, further comprising means for adjusting the threshold force by the user.

17. The muscle training device of claim 11, wherein the drive means comprises a motor; and,
the coupling means comprises a worm turned by the motor and a nut fixed to the hand grip and engaging the worm;
wherein the worm and nut provide reduction in an output of the motor to the extent that, while the motor is switched off, he user is prevented from displacing the hand grip by the force.

* * * * *

UNITED STATES PATENT AND TRADEMARK OFFICE
CERTIFICATE OF CORRECTION

PATENT NO. : 5,406,845
DATED : April 18, 1995
INVENTOR(S) : Antoine Berger and Jean-Claude Barlerin It is certified that error appears in the above-indentified patent and that said Letters Patent is hereby corrected as shown below:

In Claim 10, Column 5, line 51, delete the word "he" and insert therefor --the--.

In Claim 11, Column 6, line 13, after the word "between", insert --driving--.

In Claim 12, Column 6, line 35, delete the word "measufement" and insert therefor --measurement--.

Signed and Sealed this

Twelfth Day of September, 1995

Attest:

BRUCE LEHMAN

*Attesting Officer*   *Commissioner of Patents and Trademarks*